United States Patent [19]

Ponsold et al.

[11] 4,167,517
[45] Sep. 11, 1979

[54] GONA-4,9(10)-DIENES AND PROCESS OF PRODUCING THE SAME

[75] Inventors: Kurt Ponsold; Michael Hübner; Michael Oettel, all of Jena, German Democratic Rep.

[73] Assignee: VEB Jenapharm, Jena, German Democratic Rep.

[21] Appl. No.: 816,871

[22] Filed: Jul. 18, 1977

Related U.S. Application Data

[63] Continuation-in-part of Ser. No. 806,471, Jun. 14, 1977, abandoned.

[30] Foreign Application Priority Data

Jun. 14, 1976 [DD] German Democratic Rep. ... 193348

[51] Int. Cl.$^2$ ................................................ C07J 1/00
[52] U.S. Cl. .................... 260/397.4; 260/239.55 R; 260/397.5; 260/349
[58] Field of Search ..................................... 260/397.4; /Machine Searched Steroids

[56] References Cited

U.S. PATENT DOCUMENTS

| | | | |
|---|---|---|---|
| 3,484,464 | 12/1969 | Farkas | 260/397.4 |
| 3,506,652 | 4/1970 | Creger | 260/239.57 |

OTHER PUBLICATIONS

Journal Chem. Soc., (1964), pp. 4479–4492, by Smith et al.

*Primary Examiner*—Elbert L. Roberts
*Attorney, Agent, or Firm*—Michael J. Striker

[57] ABSTRACT

New gona-4,9(10)-dienes of formula I

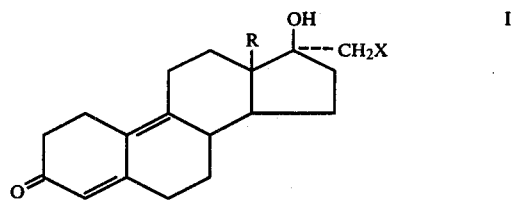

where R is alkyl of 1 to 3 carbon atoms and X is Cl, Br, F, N$_3$, SCN, CN, OH, OR'(R'=alkyl), NH$_2$, a substituted amino group or a heterocyclic compound including nitrogen in the ring. The compounds have valuable biological properties, especially hormonal and antihormonal effects, and can be used to advantage in pharmaceutical preparations for the treatment of endocrinopathies and for reproduction control in human beings and livestock.

The invention also embraces a process for making the compounds by converting 3-methyoxy-13β-R-gona-2,5(10)-diene-17β-spiro-1',2'-oxiranes first to 17β-hydroxy-17α-CH$_2$X-13β-R-gon-5(10)-en-3-one, then to the 17β-hydroxy-17α-CH$_2$X-13β-R-gona-4,9(10)-diene-3-ones of formula I.

3 Claims, No Drawings

GONA-4,9(10)-DIENES AND PROCESS OF PRODUCING THE SAME

RELATED CASES

This application is a continuation-in-part of application Ser. No. 806,471 filed June 14, 1977, now abandoned.

BACKGROUND OF THE INVENTION

The compounds that can be produced by the process according to the invention are new; their synthesis has not been described yet.

The object of the invention is the production of gona-4,9(10)-dienes according to formula I below, which in terms of biological effects are superior to comparable compounds of the prior art which are accepted in medical therapy.

The invention also has the object of providing a technologically implementable and economically acceptable process for the production of the gona-4,9(10)-dienes.

SUMMARY OF THE INVENTION

These objects are met in the following way:

3-methoxy-13β-R-gona-2,5(10)-diene-17β-spiro-1',2'-oxiranes of formula II below are opened up by appropriate nucleophilic agents in organic solvents at ordinary or elevated temperature so as to form the corresponding 3-methoxy-17α-CH$_2$X-13β-R-gona-2,5(10)-diene-17β-ols of formula III below, which in turn are hydrolyzed by a weak acid catalyst to 17β-hydroxy-17α-CH$_2$X-13β-R-gona-5(10)-ene-3-ones of formula IV below and converted into the 17β-hydroxy-17α-CH$_2$X-13β-R-gona-4,9(10)-diene-3-ones of formula I below by treatment with a halogenation agent and subsequent dehydrohalogenation. In these formulae R is alkyl of 1 to 3 carbon atoms and X is Cl, Br, F, N$_3$, SCN, CN, OH, OR'(R'=alkyl), NH$_2$, a substituted amino group or a heterocyclic compound including nitrogen in the ring.

The individual reaction steps of the process are further explained by the following sequence of formulae:

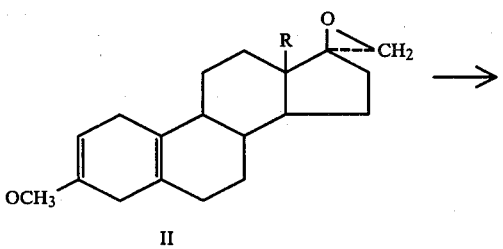

II

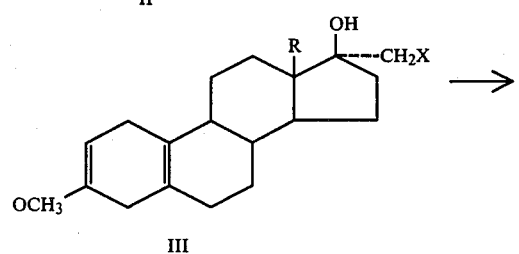

III

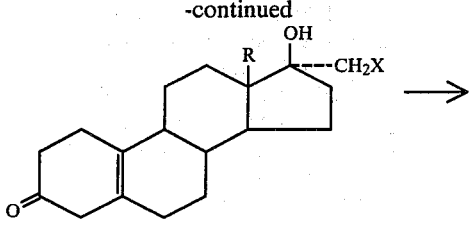

IV

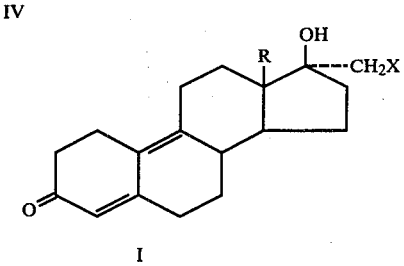

I

DETAILS AND PREFERRED EMBODIMENTS

The spiro oxiranes of formula II used as starting products are known. They can be produced, for instance, according to DL-WP No. 80 023. Sodium oxide, alkali cyanides, alkali alkoxides, alkali hydroxides, ammonia, primary and secondary amines, and nitrogenous heterocyclic compounds are preferable nucleophilic agents for the first step, which is performed under neutral or alkaline conditions.

Selection of the solvent depends on the solubility of the spiro oxirane (II) and the nucleophilic agent used and can be varied within wide limits, the object in general being a homogeneous reaction mixture. Suitable solvents are, for instance, ether, dimethylsulphoxide, ethylene glycol, ethylene glycol ether, dimethylformamide, and lower alcohols, to which minor amounts of water may be added.

The temperature at which the reaction is performed can be varied within relatively wide limits but is preferably between about 20° C. and 100° C. The opening up of the spiro oxiranes by ammonia, primary and secondary amines and nitrogenous heterocylic compounds can in many cases be accelerated by catalytic action obtained by admixture of slight quantities of a weak acid, preferably acetic acid.

Various acid catalysts are suitable for hydrolysis of the enolethers (III). Organic carboxylic acids such as acetic acid, oxalic acid, citric acid or succinic acid in dilute aqueous solution are preferably used, but dilute mineral acids such as hydrobromic acid or perchloric acid are also suitable.

Selection of the solvent depends on solubility of the substance to be hydrolyzed, with organic aqueous solvents, miscible with water, such as alcohols, dioxane or acetone, being generally preferred. It is, however, also possible, to perform the reaction in a mixture of water, a solvent miscible with water, and a solvent not miscible with water, such as water-methanol-benzene mixtures or water-tertiary butanol-methylene chloride mixtures, with the contents of the individual components in general being selected so that a homogenous phase results. The hydrolysis can, however, also be performed in a two-phase system.

The halogenation of the $\Delta^{5(10)}$-unsaturated 3-ketones (IV) obtained is preferably performed in an inert solvent at low temperature, e.g. −5° C. to +5° C. Elementary bromine is preferably used, but also perbromides such as phenyltrimethylammoniumperbromide or pyridiniumperbromide, and other halogenating agents can be used. Suitable solvents are especially chlorinated aliphatic hydrocarbons such as methylene chloride, carbon tetrachloride and chloroform, but also tertiary organic nitrogenous bases such as pyridine, possibly together with the solvents stated, can be used. Tertiary organic bases such as pyridine, the picolines, collidine, ethyl pyridine, etc., are preferred as dehydrohalogenating agents. The process is performed to advantage at room temperature but possibly the dehydrohalogenation can be accelerated by slight warming.

In general, the process according to the invention is performed so that halogenation and dehydrohalogenation are executed in one reaction step without intermediate isolation of the halogenation products. In principle, however, it is also possible to produce and isolate the corresponding 5,10-dihalo compounds in some other conventional manner, and convert them by dehydrohalogenation (halogen acid removal) in a subsequent reaction step to the 4,9(10)-dienes. The compounds of formula I obtained in the process according to the invention are isolated and purified by conventional methods.

As a variation of the process according to the invention, conversion of the spiro oxiranes (II) by the nucleophilic agents is performed not, as stated above, in neutral or alkaline medium but in faintly acid medium. In that case, hydrolysis of the enolether group in 3-position is performed concurrently with the spiro epoxide being opened up under introduction of the 17α-CH$_2$X-substituent, and the 17β-hydroxy-17α-CH$_2$X-13β-R-gona-5(10)-ene-3-one (IV) are obtained in one reaction step. This process variant can be used to special advantage in the production of formula I compounds where X, for instance, stands for Br, Cl or SCN. For that purpose, the spiro epoxides are dissolved in a suitable solvent, preferably dimethylformamide, methylene chloride, ether, or dimethylsulphoxide, and treated with dilute solution of hydrochloric acid, hydrobromic acid or rhodanic acid in the same solvent. The Δ$^{5(10)}$-diene-3-ketones (IV) obtained by this process are isolated and purified according to conventional methods.

Progestational activities are determined according to the McPhail method (R. I. Dorfmann: Methods in Hormone Research, Vol. II, Academic Press New York and London 1962). The extent of the secretory (transformatory) conversion of the endometrium of infantile rabbits, which was evaluated according to McPhail in steps from 0 to 4 to an accuracy of 0.5 units, was taken as the parameter of progestational activity. Activity was specified in the McPhail test in terms of the ED (McPhail 2), defined as the total dose in mg/kg that caused a transformation of the proliferated endometrium according to stage 2. The McPhail data were checked with the Kruskal-Wallis test. The significance statements refer to comparison of the individual groups with the Dunn test.

Table 1 shows the results of the McPhail test, after oral application, for several chracteristic representatives of the compounds of the invention. Table 2 contrasts these data, along with those obtained after subcutaneous application, with the ED (McPhail 2) data of some selected standard progestational compounds.

It is apparent that, for instance, the two compounds of general formula I where X=CN, R=CH$_3$, and X=N$_3$, R=CH$_3$, are highly efficient progestational compounds with oral and subcutaneous applications. When applied orally, the most effective of them (X=CN, R=CH$_3$) is, in terms of ED (McPhail 2), about 200 times more effective than norethisteroneacetate, 58 times more effective than ethinodioldiacetate, and 9 times more effective than d-norgestrel.

Table 1

| | Progestational activity of compounds of general formula I in case of oral application | | | | | | |
|---|---|---|---|---|---|---|---|
| Compound | Group | Total dose (4d)mg/kg BW | n | PcPhail value X | Significance compared to group | Variations Scope | Ed(McPahil 2) mg/kg |
| Sesame oil | 1 | — | 6 | 0 | — | 0 | |
| I,X=N$_3$, R=CH$_3$ | 2 | 0.05 | 6 | 1.33 | | 1.0–1.5 | |
| " | 3 | 0.10 | 6 | 1.58 | 1(+);2(+); | 1.0–2.5 | |
| " | 4 | 0.20 | 6 | 1.92 | 1(+++);3(+); | 1.0–2.5 | 0.4 |
| " | 5 | 0.40 | 5 | 2.00 | 1(+);4(+); | 1.5–3.0 | |
| I,X=CN, R=CH$_3$ | 6 | 0.025 | 6 | 0.50 | 1(+) | 0–1.0 | |
| " | 7 | 0.05 | 6 | 2.00 | 1(+);9(+); | 1.5–3.0 | |
| " | 8 | 0.10 | 6 | 2.58 | 1(+);7(+); | 1.5–3.0 | 0.05 |
| " | 9 | 0.20 | 6 | 2.91 | 1(+);8(+++); | 2.5–3.5 | |

BE = body weight
n = number of test animals
d = day

Table 2:

Comparison of progestational activities of selected steroids in case of oral and subcutaneous application

| Compound | ED(McPhail 2) p.o. | mg/kg BW s.c. |
|---|---|---|
| Norethisterone | — | 5.55 [130]) |
| Norethisteroneacetate | >10 | — |
| Ethinodioldiacetate | 2.9 | — |
| d-norgestrel | 0.45 | 0.25 +) |
| I, X = N$_3$, R = CH$_3$ | 0.40 | 0.105 |
| I, X = CN, R = CH$_3$ | 0.05 | >0.01 |

+) according to R.A. Edgren et al., Int. J. Fert., Vol. 11, p. 389 (1969)

The embodiments described below are to explain the process according to the invention without restricting it in any way.

EXAMPLE 1

17α-azidomethyl-17β-hydroxy-13β-methyl-gona-4,9(10)-diene-3-one

1st stage: 3.0 g (0.01 mole) of 3-methoxy-13β-methyl-gona-2,5(10)-diene-17β-spiro-1',2'-oxirane are suspended in 200 ml of ethylene glycol and, after addition of 5.0 g of sodium azide, heated for 6 hours on boiling water bath. The steroid dissolves at first and precipitates again with progressing reaction. The preparation is cooled and then poured into about 1,500 ml of ice water. The colorless crude product is sucked off and thoroughly washed with water. Recrystallization from methanol yields colorless needles with a melting point at 123° to 124° C., $[\alpha]_D^{25}+81°$ (C=0.5 chloroform).

Yield: 3.30 g (95 percent).

2nd stage: 1.72 g (0.005 mole) of the 17α-azidomethyl-13β-methyl-3-methoxy-gona-2,5(10)-diene-17β-01 obtained in the preceding stage are suspended in 100 ml of methanol, and a solution of 1.0 g of oxalic acid in 5 ml of water is added while cold. When shaken from time to time, the substance dissolves completely within about 90 minutes. After 2 hours the solution is poured into ice water, the flocculent crude product is sucked off, washed thoroughly with water, and dried in the desiccator. The yield is 1.42 g (85 percent).

Recrystallization from isopropyl ether yields an analytically pure product with melting point at 105° C., $[\alpha]_D^{25}+119°$ (C=0.5 chloroform).

3rd stage: 1.32 g (0.004 mole) of the 17α-azidomethyl-17β-hydroxy-13β-methyl-gona-5(10)ene-3-one obtained in the preceding stage are dissolved in 10 ml of pyridine, cooled to 5° to 10° C. and mixed with a solution of 1.5 g of pyridiniumperbromide in 12 ml of pyridine. The preparation is first stirred for 30 minutes at that temperature, then for 2 to 4 hours at room temperature, and at last poured into 100 ml of ice-cooled 2 n hydrochloric acid. The precipitated yellowish crude product is sucked off, thoroughly washed with water and, while still humid, recrystallized from methanol. 17α-azidomethyl-17β-hydroxy-13β-methyl-gona-4,9(10)-diene-3-one forms colorless needles with melting point at 204° to 206° C., $[\alpha]_D^{25}-250°$ (C=0.5 chloroform).

Yield: 0.48 g (30 percent).

EXAMPLE 2

17α-azidomethyl-17β-hydroxy-13β-ethyl-gona-4,9(10)-diene-3-one

1st stage: 0.943 g (0.003 mole) of 13β-ethyl-3-methoxy-gona-2,5(10)-diene-17β-spiro-1',2'-oxirane are suspended in 70 ml of ethylene glycol, and 1.5 g of sodium azide are added. Then, the preparation is heated for about 100 hours on a boiling water bath, allowed to cool and then poured into about 1,000 ml of water. The colorless flocculent product is sucked off, washed thoroughly with water and, while still humid, recrystallized from methanol, yielding colorless needles with melting point at 157° to 159° C., $[\alpha]_D^{25}+77°$ (C=0.5 chloroform).

Yield: 0.72 g (61 percent).

2nd stage: 2.8 g (0.008 mole) of the 17α-azidomethyl-13β-ethyl-3-methoxy-gona-2,5(10)-diene-17β-01 described above are dissolved in 6 ml of benzene and mixed with 30 ml of methanol. 1.5 g of oxalic acid dihydrate in saturated aqueous solution are added, and the preparation is intensively stirred. After 1 to 2 hours the reaction is complete, then water and benzene are added, and the layers are separated. The aqueous phase is repeatedly extracted with benzene, and the combined extracts are washed with bicarbonate solution and water. The preparation is then dried over sodium sulphate, and the solvent is expelled in vacuum. The remaining yellow oil is absorbed in hot acetonitrile. Cooling results in colorless prisms with melting point at 121° to 123° C., $[\alpha]_D^{25}+116.5°$ (C=0.5 chloroform).

Yield: 1.65 g (60 percent).

3rd stage: 3.1 g (0.009 mole) of the 17α-azidomethyl-17β-hydroxy-13β-ethyl-gona-5(10)-ene-3-one described above are dissolved in 50 ml of pyridine and cooled to 0° C. 1.58 g of bromine, dissolved in 10 ml of methanol, are added to the solution dropwise. The solution is stirred for 30 minutes at 0° C., then for 3 to 4 hours at room temperature, and then poured into about 1,000 ml of ice-cold 2 n hydrochloric acid. The colorless flocculent crude product is sucked off, thoroughly washed with water, and dried. It is dissolved in a minimum of chloroform at boiling point and then filtered. After cooling, the same or up to double the quantity of methanol is added. 17α-azidomethyl-17β-hydroxy-13β-ethyl-gona-4,9(10)-diene-3-one crystallizes in small prisms with melting point at 223° to 226° C., $[\alpha]_D^{25}-224°$ (C=0.5 pyridine).

Yield: 2.26 g (73 percent).

EXAMPLE 3

17α-cyanomethyl-17β-hydroxy-13β-methyl-gona-4,9(10)-diene-3-one

1st stage: 15.0 g (0.05 mole) of 3-methoxy-13β-methyl-gona-2,5(10)-diene-17β-spiro-1',2'-oxirane are dissolved in 500 ml of ethanol and mixed with a solution of 50 g of potassium cyanide in 100 ml of water. The solution is stirred at room temperature until the thin-layer chromatogram does not any longer indicate the presence of any starting material, which process will taken about 2 days. The mass is then cautiously mixed with 200 to 300 ml of water and left standing overnight. The precipitated product is sucked off, washed carefully, and dried in the open air. Recrystallization from acetonitrile yields colorless crystals, which melt at 145° to 151° C. and contain ½ mole of crystal ethanol.

Yield: 10.7 g (61 percent).

2nd stage: 9.8 g (0.03 mole) of the 17α-cyanomethyl-13β-methyl-3-methoxy-gona-2,5(10)-diene-17β-01 obtained according to the foregoing procedure are suspended in 400 ml of methanol and mixed with a solution of 4.0 g of oxalic acid dihydrate in 25 ml of water. The preparation is stirred at room temperature until there is no residue and starting compound is no longer indicated in the thin-layer chromatogram (3 to 6 hours). The preparation is poured into about 2,000 ml of ice water and left standing overnight. The colorless flocculent product is sucked off and dried on the air. It is sufficiently pure for further conversion.

Yield: 8.5 g (90 percent).

An analytically pure product is obtained by recrystallization from 85-percent isopropanol. Melting point at 167° to 169° C., $[\alpha]_D^{25}+155.4°$, (C=0.5 chloroform).

3rd stage: 3.44 g (0.011 mole) of the 17α-cyanomethyl-17β-hydroxy-13β-methyl-gona-5(10)-ene-3-one obtained in the preceding stage are dissolved in 15 ml of pyridine and slowly mixed with a solution of 4.0 g of pyridiniumperbromide in 35 ml of pyridine. The preparation is stirred for 90 minutes at room temperature, and the reaction mixture is then poured into about 400 ml of ice-cold 2 n hydrochloric acid. The yellowish flocculent product is sucked off, thoroughly washed with water, and dried in air. Crude yield: 2.35 g. Recrystallization from acetic ester and 80-percent acetonitrile yields needles with melting point at 209° to 214° C., $[\alpha]_D^{25}-290°$ (C=0.5 pyridine).

Yield: 1.4 g (32 percent).

EXAMPLE 4

17α-bromomethyl-17β-hydroxy-13β-methyl-gona-4,9(10)-diene-3-one

1st stage: 5.96 g (0.02 mole) of 3-methoxy-13β-methyl-gona-2,5(10)-diene-17β-spiro-1',2'-oxirane are dissolved in 200 ml of dimethylformamide, and then 5 ml of 48 percent hydrobromic acid in 50 ml of the same solvent are added in one step. The solution is stirred for 2 minutes and then immediately poured into about 1,000 ml of ice water. The colorless flocculent product is sucked off, amply washed with water, and dried in the air. Recrystallization from benzene yields colorless crystals with melting point at 127° to 129° C., $[\alpha]_D^{25} +109°$ (C=0.5 chloroform).

Yield: 4.1 g (56 percent).

2nd stage: 1.1 g (0.003 mole) of the 17α-bromomethyl-17β-hydroxy-13β-methyl-gona-5(10)-ene-3-one obtained in the preceding stage are dissolved in 20 ml of pyridine and cooled to 0° C. The solution is stirred and a solution of 0.60 g of bromine in 5 ml methanol is slowly added dropwise. Stirring continues for 30 minutes at 0° C. and then from 2 to 4 hours at room temperature. Thereafter the solution is stirred into 500 ml of ice-cold 2 n hydrochloric acid. The faintly yellowish flocculent product is sucked off, washed with water, and dried in the desiccator. Recrystallization from 90 percent acetonitrile yields 17α-bromomethyl-17β-hydroxy-13β-methyl-gona-4,9(10)-diene in the form of sturdy prisms with melting point at 119° to 123° C., $[\alpha]_D^{25} -271.3°$ (C=0.5 chloroform).

Yield: 0.41 g (37 percent).

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A compound of the formula

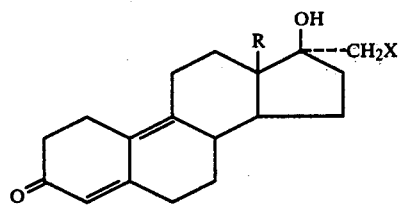

wherein R is methyl and X is $N_3$ or CN.

2. The compound of claim 1 which is 17α-azidomethyl-17β-hydroxy-13β-methyl-gona-4,9(10)-diene-3-one.

3. The compound of claim 1 which is 17α-cyanomethyl-17β-hydroxy-13β-methyl-gona-4,9(10)-diene-3one.

* * * * *